United States Patent [19]

Gordon et al.

[11] Patent Number: 4,661,509

[45] Date of Patent: Apr. 28, 1987

[54] METHODS FOR TREATING LEUKOPENIA

[76] Inventors: Arnold Z. Gordon, 5129 Mayview Rd., Lyndhurst, Ohio 44124; Arthur H. Rossof, 4334 No. Hazel - 1301, Chicago, Ill. 60613

[21] Appl. No.: 582,068

[22] Filed: Feb. 21, 1984

Related U.S. Application Data

[60] Continuation-in-part of Ser. No. 425,460, Sep. 28, 1982, abandoned, which is a division of Ser. No. 291,062, Aug. 7, 1981, abandoned.

[51] Int. Cl.$^4$ .................... A61K 31/415; A61K 31/14
[52] U.S. Cl. .................................. 514/397; 514/102; 514/103; 514/143; 514/385; 514/396; 514/408; 514/410; 514/412; 514/423; 514/461; 514/471; 514/642; 514/643; 514/579; 514/595; 514/646

[58] Field of Search ............... 514/642, 643, 102, 103, 514/143, 385, 396, 408, 410, 412, 423, 461, 471, 579, 595, 646

[56] References Cited

PUBLICATIONS

Prane—Chem. Abst., vol. 78 (1973) p. 119294z.
Arutyunova et al.—Chem. Abst., vol. 67 (1967) p. 79413b.
Stepanyan et al.—Chem. Abst., vol. 67 (1967) p. 40751k.

Primary Examiner—Sam Rosen
Attorney, Agent, or Firm—Niblack & Niblack

[57] ABSTRACT

A method of improving the levels of formed blood elements in a patient having disease or therapy induced leukopenia comprising administering to said patient a therapeutically effective amount of a pharmaceutically acceptable, water or lipid soluble tertiary or quaternary amine having cholinergic or anticholinesterase activity.

8 Claims, No Drawings

METHODS FOR TREATING LEUKOPENIA

CROSS-REFERENCE TO RELATED APPLICATIONS

This application is a continuation-in-part of our Ser. No. 425,460 filed Sept. 28, 1982 which was a division of Ser. No. 291,062 filed Aug. 7, 1981, both now abandoned.

BACKGROUND OF THE INVENTION

Many animals, including humans, under certain conditions exhibit a low immune function level and/or an inability to provide the necessary or beneficial amounts of formed blood elements in the blood. In addition, a number of diseases such as Felty's syndrome for example, can cause the same phenomenon to be observed. And, of course, in therapeutic regimens using chemotherapuetic and/or radiation therapy, one of the deleterious side effects is the myelosuppression and/or immunosuppression caused by these therapeutic regimens. Thus, regimens of the chemotherapeutic and/or radiation therapy mode are frequently limited by the myelosuppression and/or immunosuppression toxicity factor. Likewise, in many diseases, suppression of the formed blood elements content of the blood is an effect of the disease which can be as serious, if not more so, than the other effects of said diseases.

It is known that certain lithium compounds tend to counteract the myelosuppression, immunosuppression and/or neutropenia caused by a number of diseases and the regimens encompassing chemotherapeutic and/or radiation therapies. For example, see "Lithium Effects on Granulopoiesis and Immune Function", Rossof and Robinson, Plenum Press (1979), pages 79–144. The problem with using lithium compounds, however, is that the therapeutic index is too narrow.

Accordingly, it is an object of the present invention to enhance the immune response and/or the formed blood elements content of the blood in warm blooded mammals, by administering an effective amount of a water and/or lipid soluble tertiary or quaternary ammonium compound having parasympathomimetic effect at physiologic pH to said mammalian host in cases where disease and/or radiation and/or chemotherapy is causing, has caused or may cause myelosuppression and/or neutropenia, an inhibition of granulopoiesis, and/or a dimunition of immune function. In addition, it is also an object of the present invention to provide a method whereby a water and/or lipid soluble tertiary or quaternary ammonium compound can be used in an effective amount as an adjuvant to chemotherapuetic and/or radiation therapy regimens such that myelosuppression and/or immunosuppression caused by these regimens is decreased. This may allow the use of larger doses of radiation and/or drug therapy or more frequent dosage regimens and/or more quickly restoring the immune, myelopoietic and/or granulopoietic functions of mammalian patients undergoing such regimens.

SUMMARY OF THE INVENTION

The present invention provides compositions and methods of treating and/or reducing the incidence of disease and/or treatment-induced myelosuppression and/or immunosupression wherein a therapeutically effective amount of a pharmaceutically acceptable, water and/or lipid soluble tertiary or quaternary ammonium compound is adminstered to a patient in need of such treatment to regulate formed blood elements, myelostimulation, myelopoiesis, granulopoiesis and/or immune function, said water and/or lipid soluble tertiary or quaternary ammonium compound represented by the general formulae:

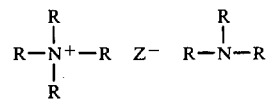

wherein each R is the same or different member of the group consisting of hydrogen or an organic group having from 1 to 30 carbon atoms with the limitation that at least one R is not only hydrogen, and wherein said R's, taken together, may form a saturated or unsaturated homocylic and/or heterocyclic ring, optionally containing a nitrogen atom; and wherein Z is a counter ion which forms a pharmaceutically acceptable salt or compound having a net charge of zero.

Compounds used in the practice of the present invention may be administered orally, intravenously, intraperitoneally, intramuscularly, subcutaneously, transdermally, or by suppository.

DETAILED DESCRIPTION OF PREFERRED EMBODIMENTS

The tertiary or quaternary ammonium compounds suitable for use in the present invention are pharmaceutically acceptable tertiary or quaternary ammonium compounds which are water soluble, lipid soluble or soluble in both water and lipids, and which exhibit cholinergic or anti-cholinesterase activity at physiologic pH. The limiting criteria is, obviously, the medical effectiveness and the therapuetic index of the particular soluble tertiary or quaternary ammonium compound.

Compounds useful in the practice of this invention are tertiary and quaternary ammonium compounds represented by the formulae:

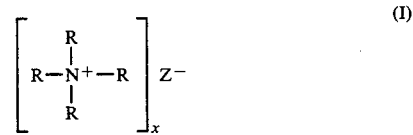

wherein each R is the same or different member of the group consisting of hydrogen or a straight, branched chain, homocyclic, or heterocyclic organic group containing from 1 to 30 carbon atoms, or two or more R groups may be combined to form a saturated or unsaturated homocyclic or heterocyclic ring; Z is a suitable counter ion such that the net charge of the compounds is zero; and x is an integer from 1 to 4.

Preferred therapeutic agents useful in the practice of the present invention are tertiary or quaternary amines having cholinergic activity or anticholinesterase activity at physiological pH. The preferred agents include compounds of Formulae III–IX:

A. Quaternary amines having cholinergic activity represented by Formula III

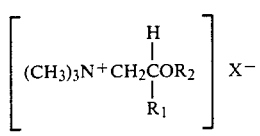 (III)

wherein $R_1$ is hydrogen or lower alkyl, $R_2$ is hydrogen, lower alkyl,

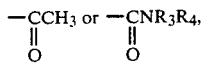

$R_3$ and $R_4$ being hydrogen or lower alkyl, and X is a negative ion such as chloride.

Preferred compounds represented by Formula III include choline, acetylcholine, methacholine, carbechol, and bethanechol.

B. Tertiary or quaternary naturally occuring or synthetic alkaloids having cholinergic activity are represented by Formulae IV and V:

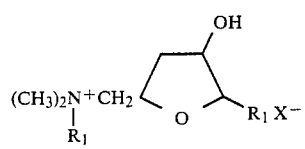 (IV)

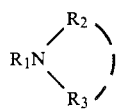 (V)

wherein $R_1$ is hydrogen, lower alkyl,

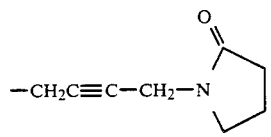

or or an unbonded electrical pair, and $R_2$ and $R_3$ taken together form a 5 or 6 membered heterocyclic ring selected from the group consisting of

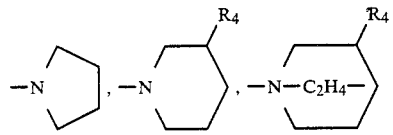

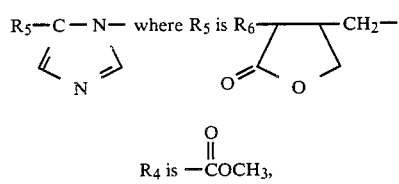

$R_4$ is $-\overset{O}{\underset{\|}{C}}OCH_3$, and $R_6$ is hydrogen or lower alkyl.

Compounds embraced by Formula V include arecoline, aceclidine, pilocarpine and oxytremarine.

C. Tertiary or quaternary ammonium anticholinesterase agents represented by Formulae VI–XI:

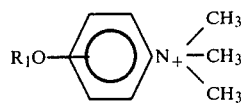 VI wherein $R_1$ is hydrogen, lower alkyl,

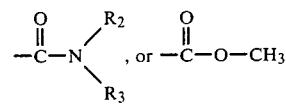

wherein $R_2$ and $R_3$ each may be hydrogen or lower alkyl.

Compounds embraced by Formula VI include neostigmine and edrophonium.

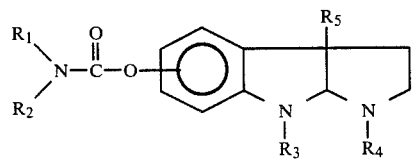 (VII)

wherein $R_1$, $R_2$, $R_3$, $R_4$ and $R_5$ are hydrogen or lower alkyl Included in compounds of Formula VII is physostigmine.

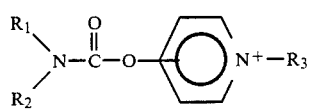 (VIII)

wherein $R_1$, $R_2$ and $R_3$ are hydrogen or lower alkyl. Included in compounds of Formula VIII is pyridostigmine.

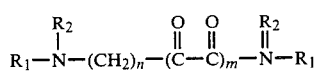 (IX)

wherein $R_1$ is either:

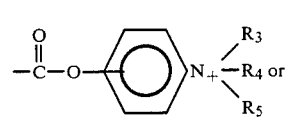

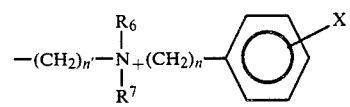

wherein $R^2$ is hydrogen or lower alkyl, $R^3$, $R^4$ and $R^5$ are the same or different members of the group consisting of hydrogen or lower alkyl, n and n' are integers from 1 to 15, m is an integer from 0 to 2, $R^6$ and $R^7$ are hydrogen or lower alkyl and X is halo or nitro. Included in the compounds of formula IX are demarcarium and ambenonium.

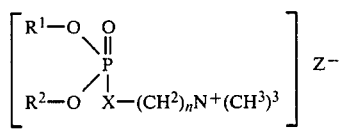

(X)

wherein $R^1$ and $R^2$ are hydrogen or lower alkyl, Z is an anion, X is O or S and n is an integer from 1 to 15. Compounds embraced by Formula X include diethoxyphosphinolthiocholine iodide.

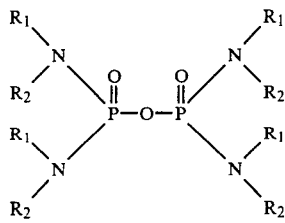

XI wherein $R_1$ and $R_2$ are hydrogen or lower alkyl. Compounds embraced by Formula XI include octamethyl pyrophosphoramide.

The preferred compounds useful in the practice of the present invention include choline, acetylcholine, methacholine, carbachol, bethanecol, muscarine, arecoline, carbamylcholine, aceclidine, pilocarpine, oxytremarine, neostigmine, edrophonium, physostigmine, pyridostigmine, demarcarium, ambenonium, octamethyl pyrophosphoramide, and diethoxyphosphinylthiocholine iodide.

Particularly preferred compounds useful in the practice of the present invention for increasing peripheral white blood cell count (WBC) are neostigmine, choline, bethanechol and pilocarpine, with neostigmine being the present drug of choice.

Choline and neostigmine are presently preferred for augmenting blood platelet counts.

The following examples further illustrate the present invention.

EXAMPLE 1

To determine the effect of representative tertiary and quaternary amines on white blood cell count, pilocarpine, a bicylic, naturally occuring tertiary amine alkaloid having cholinergic activity, choline chloride, a linear, acyclic quaternary amine having cholinergic activity and neostigmine, a monocyclic quaternary amine having anticholinesterase activity were tested against lithium carbonate as the positive control and saline as the negative control to determine the effects on the hematologic status of the test animals.

For each drug and control, groups of 20 mice received a daily 1 cc intraperitoneal injection for ten consecutive days. The dosages are set forth in Table I.

TABLE I

| Drug | Dosage (mg/kg) |
| --- | --- |
| Pilocarpine | 26 |
| Choline chloride | 40 |
| Neostigmine | 0.5 |
| Lithium carbonate (positive control) | 60 |
| Saline (negative control) | |

Mice were serially sacrified on days 4, 6, 8 and 10 and blood parameters determined with the following results.

TABLE II

| Increase in Peripheral While Blood Cell Counts | |
| --- | --- |
| DRUG | PERCENT INCREASE |
| Neostigmine | +120% |
| Choline chloride | +83% |
| Pilocarpine | +107% |
| Lithium carbonate | +123% |
| Saline | 0 |

TABLE III

| Increase in Peripheral Blood Platelet Counts | |
| --- | --- |
| DRUG | PERCENT INCREASE |
| Neostigmine | +8% |
| Choline chloride | +5% |
| Pilocarpine | +1% |
| Lithium carbonate | +45% |
| Saline | 0 |

Compounds useful in the practice of the present invention generally may be administered via oral, intravenous, transdermal, intramuscular, intraperitoneal, subcutaneous, suppository, or submucosal routes of administration depending upon the patient, and the particular therapeutic agent employed, consistent with the bounds of standard medical practice, as discussed below.

The compositions and methods of the present invention are employed in cases where a pathological consequence of a disease is either myelosuppression or neutropenia or other blood constituent count reduction. An example of this type of disease is Felty's syndrome, anemia, and the like.

Further, in those diseases where the regimen used to treat the disease causes a deleterious side effect of neutropenia, myelosuppression, a diminution of formed blood elements content of the blood and/or an impairment or lowering of the immune function, said deleterious effect may be treated either prophylactically or as adjunctive therapy or following cessation of the drug or radiation therapy which led to the need for such treatment as discussed in detail below. Typical examples are, for example, employing the methods of the present invention as an adjuvant to chemotherapy regimens and/or radiation regimens in the treatment of cancers. Lithium is presently employed, but its use is limited by its narrow therapeutic index.

The amount of the compounds employed in the practice of the present invention which is administered will be determined by the species of mammalian patient being treated, the particular physiology of the patient, the solubility of the compound selected, the therapeutic index of the compound, and the level to which the immune function, granulopoiesis, neutropenia, diminution of the formed blood elements content of the blood and/or myelosuppression of immune suppression are within said patient. Dosages and routes of administration for the preferred compounds of the present invention are discussed below.

In the practice of the present invention, the tertiary or quaternary ammonium compounds selected for use in a particular treatment are preferably administered orally, subcutaneously or transdermally. The dosage selected will depend upon the drug selected, the particularly physiology of the patent undergoing treatment, and the like. While non-subcutaneous parenteral administration can be employed in appropriate cases, care must be taken because of the possibility of serious cardiovascular effects. For example, the non-subcutaneous parenteral administration of as little as 0.1 mg/kg iv of pilocarpine, produces a complex cardiovascular response. Such an untoward toxicity may be counteracted with atropine sulfate (0.5 to 1.0 mg i.m. or i.v.) Non-subcutaneous parenteral administration should be selected with care when the patient cannot tolerate alternate dosage forms, i.e. 5–10 mg of pilocarpine via oral administration.

Choline on the other hand is relatively non-toxic and can be tolerated in amounts of up to 6 grams daily. Bethanechol, on the other hand, while orally active at dosages of 30–200 mg daily, preferably in 3–4 divided doses, should not be administered by the non-subcutaneous parenteral route. Neostigmine is tolerated in oral dosages of 15–375 mg as the bromide, while parenteral dosages are generall 1/30 that of oral dosages.

The ability of tertiary and quaternary ammonium compounds with cholinergic or anticholinesterase activity to modulate hematologic values may have a significant impact on cancer therapy where a combination of chemotherapy or radiation therapy and the disease itself wreak havoc on the patient's blood picture and immune system.

Thus, in one embodiment of the present invention, cytotoxic therapy alone is administered during the first portion of the clinical cycle to a patient with malignancy. This administration would lower peripheral blood counts by having decreased the amount of healthy hematologic tissue.

During the second portion of the therapeutic cycle, i.e., the second two of a prototypical four week repeating therapeutic regimen, a parasympathomimetic(cholinergic or anticholinesterase) agent is administered to augment the rate of recovery of healthy hematological tissues such as white blood cells.

In another embodiment of the present invention, patients with, for example, Felty's Syndrome are treated with, for example, pilocarpine. This administration results in an elevation of circulating white blood cell counts and an augmentation of myelopoiesis.

In view of the myleosuppressive side effects of therapeutic radiation, numerous commonly used drugs, such as anti-neoplastics, antibiotics, and others which can depress white blood cell count, particularly on chronic administration, the discovery that tertiary and quaternary ammonium compounds having parasympathomimetic or cholinergic and/or anticholinesterase activity are useful in enhancing production of white blood cells, and selectively modifying the blood picture is a significant, pioneering development in the medical field.

The invention claimed is:

1. A method of increasing the peripheral white blood cell count in a patient having disease or therapy induced leukopenia comprising administering to said patient a therapeutically effective amount of a pharmaceutically acceptable, water or lipid soluble tertiary or quaternary amine having cholinergic or anti-chlolinesterase activity.

2. The method of claim 1 wherein said tertiary or quaternary amine is administered to a patient in need of said treatment via oral administration.

3. The method of claim 1 wherein said tertiary or quaternary amine is administered to said patient in need of said treatment via transdermal administration.

4. The method of claim 1 wherein said tertiary or quaternary amine is administered to said patient in need of said said treatment via subcutaneous administration.

5. The method of claim 1 wherein said tertiary or quaternary amine is selected from the group consisting of choline, acetylcholine, methacholine, carbachol, bethanacol, muscarine, arecoline, carbamylcholine, aceclinidine, pilocarpine, oxytremarine, neostigmine, edrophonium, physostigmine, pyridostigmine, demarcarium, ambenonium, octamethyl pyrophosphoramide, and diethyloxyphosphinylthiocholine or a pharmaceutically acceptable salt thereof.

6. The method of claim 1 wherein said compound is pilocarpine.

7. The method of claim 1 wherein said compound is neostigmine.

8. The method of claim 1 wherein said compound is choline.

* * * * *